United States Patent [19]

Rothermel et al.

[11] 4,255,820
[45] Mar. 17, 1981

[54] ARTIFICIAL LIGAMENTS

[76] Inventors: Joel E. Rothermel, 55 Central Park West, New York, N.Y. 10023; Robert J. Pawluk, 8 Valemont Rd., Montvale, N.J. 07645

[21] Appl. No.: 60,221

[22] Filed: Jul. 24, 1979

[51] Int. Cl.³ .............................................. A61F 1/00
[52] U.S. Cl. ........................................ 3/1; 128/92 C
[58] Field of Search ............................. 3/1, 1.9, 1.91; 128/92 C

[56] References Cited

U.S. PATENT DOCUMENTS

| | | | |
|---|---|---|---|
| 3,176,316 | 4/1965 | Bodell | 3/1 |
| 3,513,484 | 5/1970 | Hausner | 3/1 |
| 3,545,008 | 12/1970 | Bader, Jr. | 3/1 |
| 3,577,837 | 5/1971 | Bader, Jr. | 3/1 |
| 3,613,120 | 10/1971 | McFarland, Jr. | 3/1 |
| 3,646,615 | 3/1972 | Ness | 3/1 |
| 3,681,786 | 8/1972 | Lynch | 3/1 |
| 3,797,047 | 3/1974 | Pillet | 3/1 |
| 3,805,300 | 4/1974 | Tascon-Alonso | 3/1 |
| 3,842,441 | 10/1974 | Kaiser | 3/1 |
| 3,855,638 | 12/1974 | Pilliar | 3/1.9 X |
| 3,877,080 | 4/1975 | Olcott | 3/1 |
| 3,886,600 | 6/1975 | Kahn et al. | 3/1 |
| 3,896,500 | 7/1975 | Rambert et al. | 3/1 |
| 3,953,896 | 5/1976 | Treace | 3/1 |
| 3,971,670 | 7/1976 | Homsy | 3/1 X |
| 3,973,277 | 8/1976 | Semple et al. | 3/1 |
| 3,988,783 | 11/1976 | Treace | 3/1 |
| 4,127,902 | 12/1978 | Homsy | 3/1 |

Primary Examiner—Clifford D. Crowder
Attorney, Agent, or Firm—Hopgood, Calimafde, Kalil, Blaustein & Lieberman

[57] ABSTRACT

An improved artificial ligament is tubular in overall configuration with flared ends, which have a graduated pore density to permit controlled hard and soft tissue ingrowth, and a central portion which prevents tissue ingrowth. The central section of the ligament is elongatable along its longitudinal axis to permit the needed elasticity in use.

15 Claims, 1 Drawing Figure

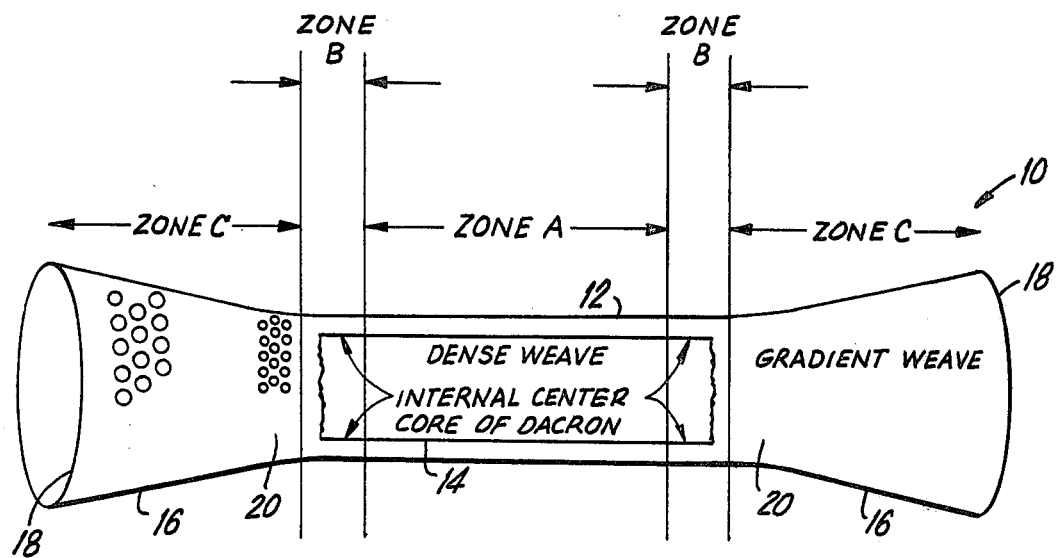

ARTIFICIAL LIGAMENTS

This invention relates generally to prosthetic devices and more particularly to a prosthetic ligament.

Prosthetic ligaments are known for the replacement or reconstruction of natural ligaments which have been destroyed either by damage or disease. These known prosthetic ligaments generally require the use of mechanical elements, such as sutures, pins or staples to attach the prosthetic device to the bone. One known prosthetic device is disclosed in U.S. Pat. No. 3,176,316 to Bodell. That patent describes a prosthetic tendon (i.e. that connects muscle to bone) which requires the use of sutures for attachment to soft tissue. However, since an artificial ligament connects bone to bone it must be elastic, and several artificial ligaments have failed because of their insufficient elasticity. Moreover, at the point of attachment to the bone, the prosthetic ligament should be substantially inelastic to prevent the ligament from becoming detached from the bone. Further, these devices, when installed in the body, are subjected to considerable amounts of tension and many of the known devices have been found to be unable to withstand the forces generated while the user moved. Finally, a number of the prior prosthetic ligament devices are insufficiently resistant to fraying during motion so that they have to be replaced periodically.

Accordingly, it is an object of this invention to provide an improved artificial ligament.

It is another object of this invention to provide an improved artificial ligament which does not require mechanical attachment to bone.

It is another object of this invention to provide an improved artificial ligament which has an elastic section.

It is another object of this invention to provide an improved artificial ligament whose design permits controlled soft and hard tissue ingrowth.

It is another object of this invention to provide an improved artificial ligament which substantially resists fraying during movement of the bone structure.

It is another object of this invention to provide an improved artificial ligament which resists extraction from the joint under functional tension.

In accordance with the present invention, a prosthetic ligament is tubular in overall configuration and has a cylindrical central section with flared sections at either end of the cylindrical portion. The central portion has a tightly woven structure to prevent tissue ingrowth and is elastic along its longitudinal axis. The central portion may also include a cylindrical insert for stress relief. Each of the flared sections employs a graduated pore structure, with smaller pores at the inner end and larger pores at the outer ends. The smaller pores permit soft tissue ingrowth while the larger pores permit hard tissue ingrowth. The graduated pore structure permits natural attachment of the prosthetic device to the bone without the need for mechanical attachment.

Still other objects of this invention will become apparent upon a reading of the detailed specification as considered with the accompanying drawing which is a schematic elevation of an improved artificial ligament constructed in accordance with the instant invention.

The prosthetic ligament of the instant invention, which is generally designated 10, is divided into three types of zones which are symmetrically arranged along the axis of the ligament. Zone A, the center segment of the ligament, crosses the joint space and is, therefore, free of any attachment to bone; intermediate zones B, which are provided at each end of zone A, are the portions of ligament 10 which enter the bone; and end zones C are the portions of ligament 10 which are attached to the bone.

Zone A is constructed from a section 12 of tubular polyester fiber having densely woven fibers of small pore size to prevent tissue ingrowth. The pore size of section 12 is in the range of 2-10 microns. Section 12 serves as a surface for fibrous tissue attachment about its perimeter which will form a sheath around section 12. The growth of the fibrous sheath of tissue about section 12 serves two purposes. First, it serves to protect the underlying fiber of section 12 from abrasion, thereby to reduce fraying. Since this sheath is replaced naturally by the body, the long-term function of ligament 10 is enhanced. Secondly, the sheath of tissue ensures a low friction surface during knee motion to further prevent wear on ligament 10.

Section 12 of zone A is formed so as to be elastic, having an elongation factor of between 4 to 6% of its length. Inserted within section 12 is a cylindrical core 14 of Dacron or other inert biologically compatible material, such as a cross-linked or vulcanized rubber, or high-density polyethylene. Core 14 is effective to maintain the tubular shape of ligament 10 and to provide strain relief throughout zone A and into zones B.

Zones B are transitional zones between elastic zone A and inelastic zones C, which provide the anchoring of prosthesic ligament 10 to the bone. Zones B are the shortest of the three zones (6-10 millimeters) and are designed to withstand fraying and fatigue at the juncture between elastic and rigid fixation which occurs when ligament 10 enters the bone at either end of the joint.

Zones C formed by sections 16 of ligament 10 are comprised of polyester fiber which is flared from a diameter of approximately 10 millimeter to an outer diameter of approximately 16 millimeters. The polyester fabric forming sections 16 is graduated in pore density to provide controlled tissue ingrowth and attachment to the bone. The extreme outer ends 18 of sections 16 contain pores between 250 and 500 microns in diameter to permit hard (bone) tissue ingrowth. In the portions 20 of sections 16 immediately adjacent zones B, the pore size is reduced to 150 to 250 microns to permit soft but not hard tissue ingrowth. The flared configuration of sections 16 serves a two-fold purpose; to provide a space for insertion of an autogenous bone graft to enhance fixation and, the large diameter end resists extraction of ligament 10 into the joint space when placed under functional tension by the patient.

Ligament 10 may be constructed from any suitable polyester or other biologically compatible synthetic textile. One suitable type of polyester is Dupont No. 56 woven with a controlled continuum of specific pore diameters for the three zones described. The specific pore size and gradient thereof elicits specific biological tissue responses, i.e. sheath formation and bone or fibrous tissue ingrowth dependent upon pore size. The controlled pore size permits the various zones of ligament 10 to function in different manners in regard to wear, fraying, fatigue, and anchoring. Zone A is provided with a stress-relieving Dacron structure 14 and a controlled degree of elongation for proper joint function. No mechanical fixation with sutures, pins or staples is required to anchor ligament 10 since its pore design provides a natural tissue fixation mechanism. Metallic markers or barium sulfate may be included in various sections of ligament 10 to enhance x-ray visualization. Carbon in various forms may also be added to increase the strength of ligament 10.

It should be noted that any dimensions given herein are for purposes of description only as the dimensions may be altered for different types of ligament replacement. The dimensions are not to be construed in any limiting sense. Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

What is claimed is:

1. A ligament prosthesis comprising:
   a central tubular portion of fabric, said central portion being elongatable along its longitudinal axis; and
   tubular end portions joined to each end of said central portion, said end portions including pores graduated in size to form a small pore structure proximate to said central portion and a larger pore structure at the end distal to said central portion, thereby to permit controlled tissue ingrowth within said end portions.

2. The ligament prosthesis as claimed in claim 1, wherein said end portions flare from a narrowest portion adjacent said central portion.

3. The ligament prosthesis as claimed in claim 1, wherein at least one of said central and said end portions comprises a woven polyester fabric.

4. The ligament prosthesis as claimed in claim 1, wherein said pore structure of said end portions proximate to said central portion is sufficient to permit ingrowth of soft tissue without permitting ingrowth of hard tissue.

5. The ligament prosthesis as claimed in claim 4, wherein said pore structure of said flared portion of said distal end is sufficient to permit ingrowth of hard tissue.

6. The ligament prosthesis as claimed in claim 5, wherein said central portion further includes a cylindrical insert.

7. The ligament prosthesis as claimed in claim 6, wherein said central portion has pores of a dimension sufficiently small to resist the ingrowh of tissue.

8. The ligament prosthesis as claimed in claim 7, further including an intermediate section joining said end section and said central section.

9. The ligament prosthesis as claimed in claim 1, wherein said pore structure of said flared portion of said distal end is sufficient to permit ingrowth of hard tissue.

10. The ligament prosthesis as claimed in claim 9, wherein said central portion further includes a cylindrical insert.

11. The ligament prosthesis as claimed in claim 10, wherein said central portion has pores of a dimension sufficiently small to resist the ingrowth of tissue.

12. The ligament prosthesis as claimed in claim 11, further including an intermediate section joining said end section and said central section.

13. The ligament prosthesis as claimed in claim 1, wherein said central portion has pores of a dimension sufficiently small to resist the ingrowth of tissue.

14. The ligament prosthesis as claimed in claim 13, further including an intermediate section joining said end section and said central section.

15. The ligaments prothesis as claimed in claim 1, wherein said central portion and said end portion are integral.

* * * * *